United States Patent

Mariani et al.

Patent Number: 5,821,425
Date of Patent: Oct. 13, 1998

[54] REMOTE SENSING OF STRUCTURAL INTEGRITY USING A SURFACE ACOUSTIC WAVE SENSOR

[75] Inventors: Elio A. Mariani, Hamilton Square; Raymond C. McGowan, Neptune, both of N.J.; James T. Stewart, Nashua, N.H.

[73] Assignee: The United States of America as represented by the Secretary of the Army, Washington, D.C.

[21] Appl. No.: 723,068

[22] Filed: Sep. 30, 1996

[51] Int. Cl.⁶ .................................................... G01L 11/00
[52] U.S. Cl. .................................................. 73/703; 73/702
[58] Field of Search .............................. 73/598, 619, 703, 73/768, 702, 704

[56] References Cited

U.S. PATENT DOCUMENTS

| | | | |
|---|---|---|---|
| 4,265,124 | 5/1981 | Lim et al. | 73/703 |
| 4,317,372 | 3/1982 | Hartemann | 73/703 |
| 4,623,813 | 11/1986 | Naito et al. | 73/703 |
| 5,235,235 | 8/1993 | Martin et al. | 73/703 |

*Primary Examiner*—Richard Chilcot
*Assistant Examiner*—Max H. Noori
*Attorney, Agent, or Firm*—Michael Zelenka; John M. O'Meara

[57] ABSTRACT

A surface acoustic wave (SAW) sensing device for remotely sensing structural integrity of a physical structure. The sensing device includes a piezoelectric substrate with a notch formed part way in the bottom of the substrate and along the width thereof. The substrate is mounted to a physical structure of interest. An antenna is coupled to the RF circuit on the substrate and is capable of receiving and transmitting a RF signal. Interdigital input and output transducers are disposed on the upper surface of the substrate. The input transducer is located adjacent one end of the substrate and the output transducer is located adjacent an opposing end of the substrate. Bus bars connect the input and output transducers. The input transducer provides a complementary first response upon receipt of an RF expanded linear/nonlinear FM signal from the antenna and transmits this compressed pulse to the output transducer. The output transducer provides a second response upon receipt of the first response and transmits the same to the antenna via the bus bar. When the substrate is strained beyond a predetermined critical level, the substrate is fractured along the notch and the first response emitted by the input transducer is prevented from being transmitted to the output transducer indicating SAW sensor failure and that structural integrity has been compromised.

14 Claims, 3 Drawing Sheets

REMOTE SENSING OF STRUCTURAL INTEGRITY USING A SURFACE ACOUSTIC WAVE SENSOR

STATEMENT OF GOVERNMENT INTEREST

The invention described herein may be manufactured, used, sold, imported and licensed by or for the. Government of the United States of America without the payment to us royalty thereon.

FIELD OF THE INVENTION

The present invention relates to the field of surface acoustic wave (SAW) devices, and more particularly to such devices which are adapted to remotely sense the structural integrity of physical structures.

BACKGROUND OF THE INVENTION

The level of damage to buildings, bridges and the like which may occur during catastrophic events such as hurricanes, tornadoes, earthquakes, explosions and the like, must be ascertained in order to ensure the safety of such structures. It is also necessary to periodically test structures for deformations caused by ordinary fatigue. Frequently, damage occurs in areas of structures which are not readily accessible to human inspection. Accordingly, there is a need for a sensing system capable of sensing and measuring certain predetermined physical variables, e.g. strain, at remote locations. Furthermore, it is desirable for such a system to provide strong output radio frequency (RF) signals which can be effectively transmitted to distant receivers.

SUMMARY OF THE INVENTION

Accordingly, it is an object of the present invention to provide small, passive, low cost RF SAW sensing devices that can be remotely interrogated by utilizing appropriate transceivers in order to obtain information concerning the soundness of the physical structure to which such sensing devices are attached.

This and other objects of the invention are accomplished by providing a SAW sensor which remotely senses the structural integrity of a physical structure (i.e. bridges, building, dams, etc.) by acting as a fuse. The SAW sensor would become inoperative once a critical strain threshold is surpassed. The sensing device is rigidly mounted to the structure and would be interrogated via a companion transceiver at a distance (i.e. up to 100 feet, conveniently).

The sensor includes a piezoelectric crystal substrate with interdigital transducers at the input and output that are photoetched in a thin metallic film deposited on the highly-polished top surface of the substrate. The transducers are connected by a pair of bus bars that run parallel to the length of the substrate.

An RF antenna is built into the sensor package to permit interrogation from a distance. A properly designed notch or groove is formed in the back or bottom surface of the substrate midway between the input and output transducer. The notch runs perpendicular to the acoustic signal path across the full width of the substrate and extends only part way into the thickness of the crystal as determined by proper design.

Unstrained, the SAW sensor would operate as a simple delay device with a compressive input transducer to provide processing is gain for enhancement of the incoming RF signal. When the sensor is strained beyond a predetermined critical level, the sensor substrate is designed to fracture along the notch, thus making the device inoperable. Sensor failure, thus, indicates a critical level of structural deformation has occurred.

Alternatively, a second embodiment of the present invention employs a SAW sensor with a compressive input transducer and a pair of output sensing taps spaced at a fixed, known distance or time delay. When the sensor is unstrained, the time between signals corresponding to the fixed output taps establishes a nominal reference delay time. A significant strain imparted to the rigidly mounted sensor package and substrate would cause a change in the phase velocity and a corresponding change in the delay time between taps. The resulting shift could be measured via remote RF interrogation with a companion transceiver. Again, the SAW sensor would incorporate a built-in antenna and provide processing gain (via pulse compression) for an extended interrogation range.

BRIEF DESCRIPTION OF THE DRAWINGS

These and other features and details of the invention will be better understood from the following Detailed Description of the Invention and the accompanying drawings in which.

DETAILED DESCRIPTION OF THE PREFERRED EMBODIMENT

Figure 1:
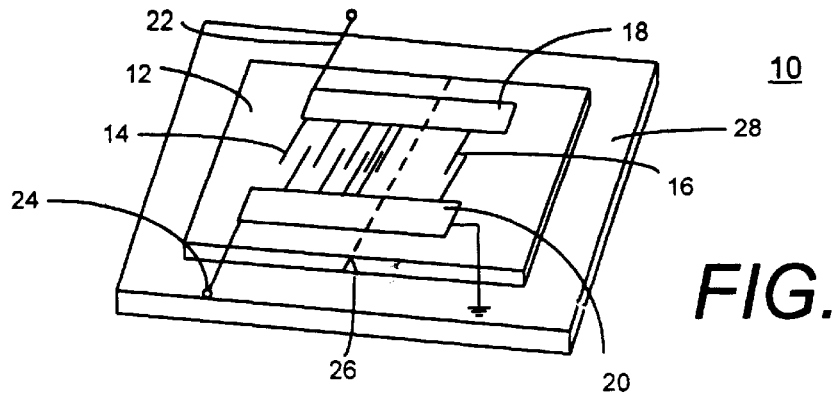
FIG. 1 is a perspective view of a SAW sensing device of the present invention with the top cover removed and a notch formed in the bottom surface thereof.

Referring to FIG. 1 there is shown a perspective view of a SAW sensing device constructed in accordance with the principles of the present invention and denoted by the numeral 10. The sensing device 10 includes a piezoelectric Surface Acoustic Wave (SAW) substrate 12 with a smooth, highly polished upper surface 13. The substrate is typically comprised of quartz or lithium niobate, but those skilled in the art will recognize that most any piezoelectric substrate will work in the present invention. An interdigital dispersive (compressive) input transducer 14 and an interdigital output transducer 16 are photoetched in thin metal films, e.g. aluminum, on the upper surface of the substrate 12. The transducers each include a number of electrodes for efficient signal injection and/or detection. A pair of bus bars 18 and 20 are positioned on the substrate 12. The bus bars 18 and 20 connect the input transducer 14 to the output transducer 16 as more fully described below.

Antennas 22 and 24 are connected to bus bars 18 and 20 and extend outwardly from the substrate 12. The antennas 22 and 24 are configured here as a simple dipole. However, it should be noted that other antenna configurations such as loop or a slot-type may be utilized, as well.

In the preferred embodiment, a notch 26 is formed in the bottom surface of the substrate 12 along the width thereof. The notch 26 is preferably located approximately midway between the input transducer 14 and the output transducer 16. The notch 26 is designed to be of a sufficient width and depth so that the substrate 12 will fracture along the notch 26 when the device 10 is subjected to a predetermined strain level.

The substrate 12 is preferably mounted on a housing 28. A top cover (not shown) is secured to the housing 28 over the substrate 12. The top cover does not contact the SAW substrate 12. The top cover and the housing 28 make up a hermetically sealed package. The entire package can be either rigidly mounted to, or positioned within, a designated structure such as a building or bridge element so that any significant deformation of the structure will cause the housing 28 and the SAW substrate 12 to be strained. If the structure is deformed beyond a predetermined critical level, the housing 28 will also become deformed, thereby causing the substrate 12 to fracture along the notch 26 formed therein.

Sensing device 10 may be fabricated as a hermetically sealed sensor package which is rigidly mounted on a structure. However, the sensor package may also be mounted inside of a structure which is to be interrogated. In all cases, though, the sensor antenna must be properly exposed (i.e. not shielded).

A transceiver unit, which may be hand held, sends a radio frequency (RF) interrogation signal which is received by sensor antennas 22 and 24. The antennas 22 and 24 would have the potential to receive signals transmitted from distances of approximately 30 meters (100 feet) with properly design SAW device. The RF signal can penetrate nonmetallic structures including concrete, glass, plastic, etc. Accordingly, the antennas 22 and 24 will pick up the signal so long as they are not shielded by a metallic structure. The transmitted signal is preferably in the form of an expanded, linear or nonlinear FM waveform.

The input transducer 14 compresses the transmitted expanded waveform into a narrow pulse, which is equal to the reciprocal of the bandwidth of the transmitted signal. The compression process at the input transducer 14 provides processing gain or signal level enhancement. The projected processing gain in this case can reach approximately 20 dB which translates into a 100 fold increase in the input signal level. Such an increase enhances the effective interrogation range for a fixed transmitted signal power or allows for a reduction in the power level of the transmitted signal. It should be noted that when the package is mounted to a structure to be interrogated, care must be taken to position the sensing device 10 in such a manner as to permit the sensor antennas to freely receive and respond to interrogation signals from the transceiver unit, which means it cannot be shielded by any metallic objects.

If the structure to which the sensing device 10 is mounted has not been strained beyond a predetermined critical level, the narrow, compressed pulse exiting from the input transducer 14 is carried to the output transducer 16 which detects and retransmits a sampled replica of the compressed pulse to the antennas via the bus bars 18 and 20. This sensor response is then received by the transceiver unit. In so doing, the acoustic signal pulse necessarily passes along the substrate surface over the notch 26 which runs perpendicular to the direction of propagation of the acoustic signal. Reception of the signal by the transceiver unit indicates that the structure has not been critically deformed.

However, if the structure has been strained beyond a critical level, the sensing device 13, which is mounted to the structure, will fracture along the notch 26. In such a case, the narrow, compressed pulse exiting the input transducer 14 will not be delivered to the output transducer 16 since the SAW device is inoperative. This lack of a response indicates that the SAW sensing device substrate 12 has been fractured, and that therefore the structure to which the sensing device 10 is mounted has been critically strained.

Figure 2:
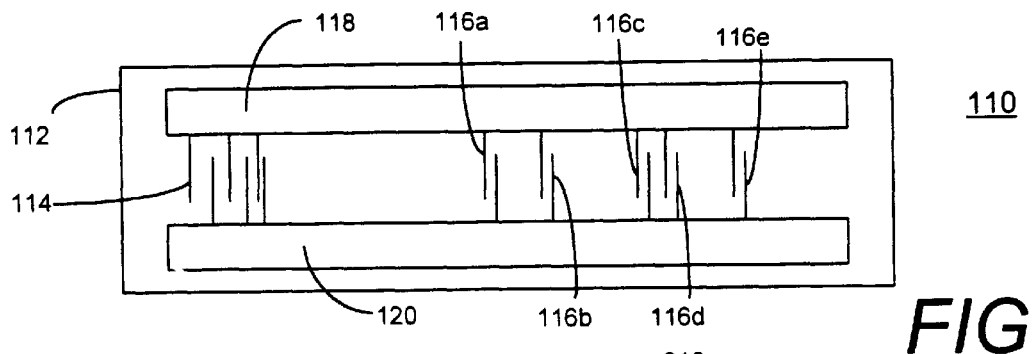
FIG. 2 is a top plan view of a SAW sensing device with the top cover removed and with several output taps spaced at precise time-ordered intervals.
Figure 2A:
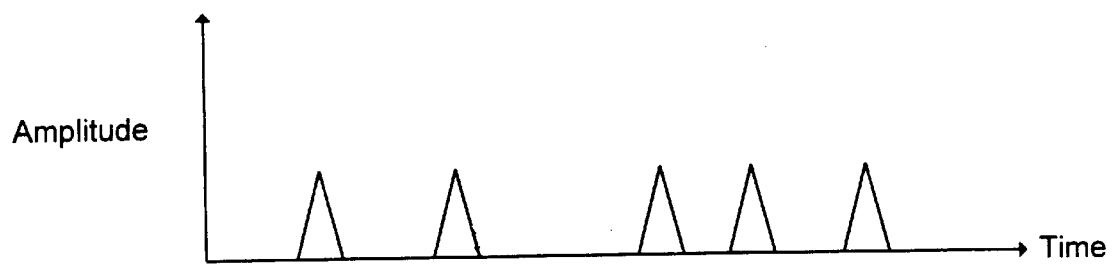
FIG. 2a is a graph showing the output pulses at each of the taps of the device shown in FIG. 2.

In order to differentiate among several SAW sensing devices that can be mounted on or in a structure which is to be interrogated, different coding methods can be utilized. For example, each sensing device can utilize several output taps spaced at precise time-ordered intervals, e.g. at defined fractions of a microsecond. FIG. 2 shows an example of such a sensing device 110 which includes a substrate 112, an input transducer 114, a plurality of output taps 116a–116f, and bus bars 118 and 120. FIG. 2a shows a time/amplitude response at the output taps of the sensing device shown in FIG. 2.

Figure 3:
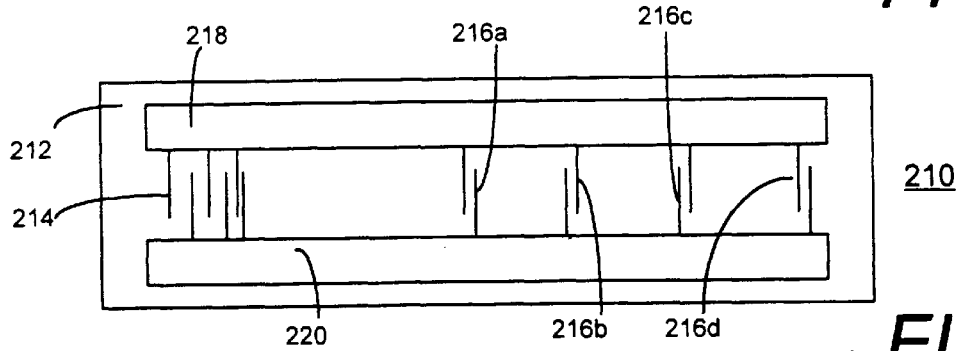
FIG. 3 is a view similar to FIG. 2 with several distinctly phase-coded output taps.
Figure 3A:
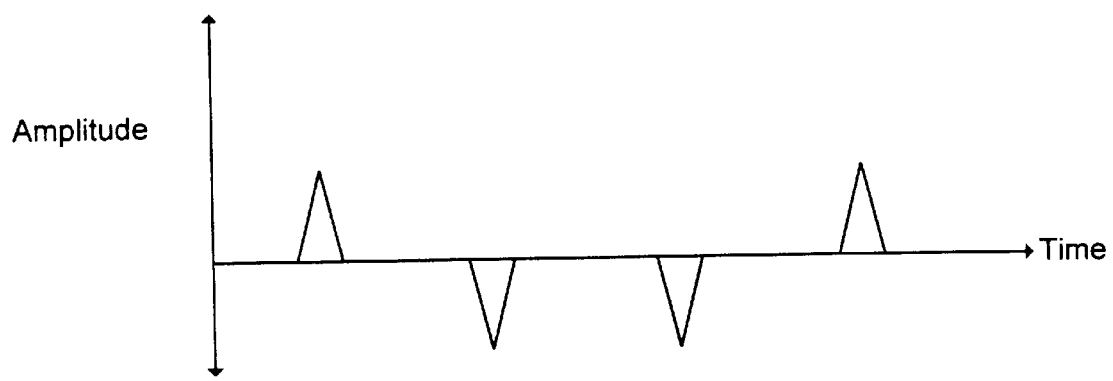
FIG. 3a is a graph showing the output pulses at each of the taps of the device shown in FIG. 3.

The output taps can also be phase-coded at 0° and 180°, essentially defined as (+) or (−). FIG. 3 shows an example of such a sensing device 210 which includes a substrate 212, an input transducer 214, a plurality of output taps 216a–216f, and bus bars 218 and 220. FIG. 3a shows a time/amplitude response at the output taps of the sensing device shown in FIG. 3, where the amplitude of the pulses vary positively and negatively corresponding to the 0° and 180° coding in the taps.

Figure 4:
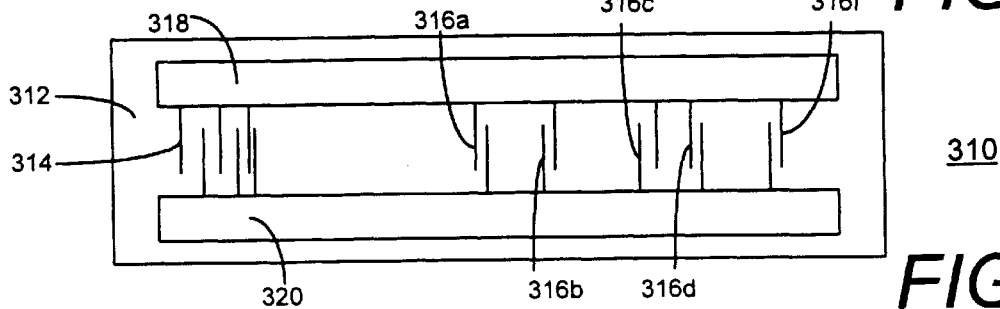
FIG. 4 is a view similar to FIG. 2 with several distinctly phase-coded output taps which are spaced at precise time-ordered intervals.
Figure 4A:
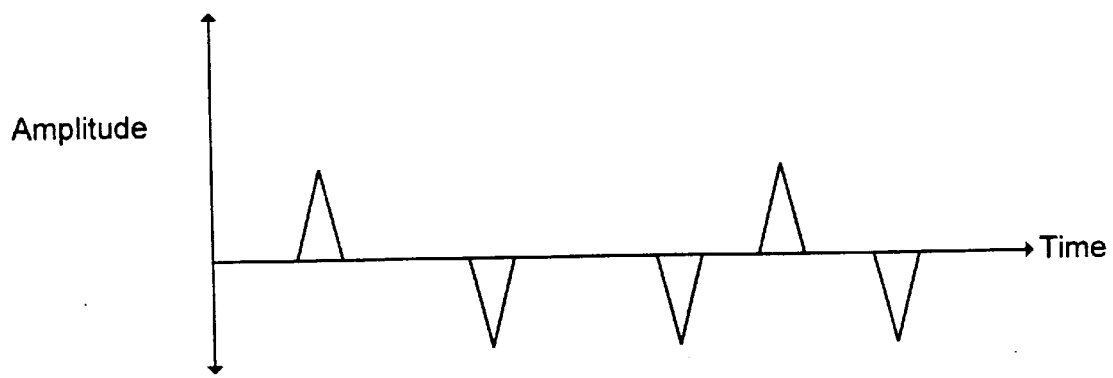
FIG. 4a is a graph showing the output pulses at each of the taps of the device shown in FIG. 4.

The two coding techniques shown in FIGS. 2 and 3 can be combined to yield a third combination output response. FIG. 4 shows an example of such a sensing device 310 which includes a substrate 312, an input transducer 314, a plurality of output taps 316a–316e, and bus bars 318 and 320. FIG. 4a shows a time/amplitude response at the output taps of the sensing device shown in FIG. 4, wherein the output provides a combination of time-ordered and phase coded pulses.

The aforementioned coding schemes provide a means for identifying the individual SAW sensing devices within a particular structure. In order to further facilitate the identification of individual sensing devices, the interrogating transmitter beam width should be limited to a few degrees.

Figure 5:
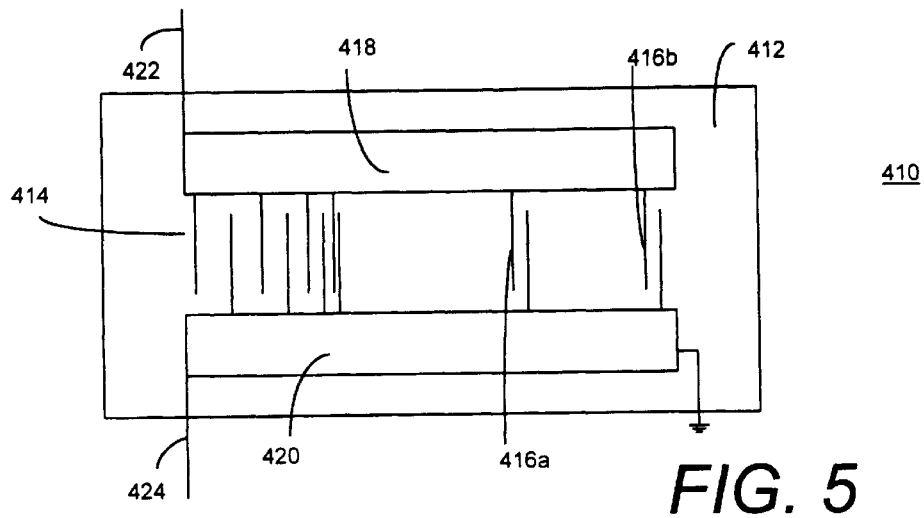
FIG. 5 is top plan view of an alternative SAW sensing device with two spaced apart output taps.

An alternative embodiment of the SAW sensing device according to the present invention is shown in FIG. 5. The sensing device 410 includes a substrate 412 which is comprised of a piezoelectric material. The substrate may be approximately about 1 cm long and 0.5 cm wide. A dispersive input transducer 414 and a pair of output sensing taps 416a and 416b are disposed on the upper surface of the substrate 412. The sensing taps 416a and 416b are spaced at a predetermined, fixed distance that corresponds to a known fixed delay time. A pair of bus bars 418 and 420 connect the input transducer 414 to the taps 416a and 416b. Antennas 422 and 424, configured in FIG. 5 as a simple dipole, are each connected to a corresponding one of the bus bars 418 and 420. The SAW sensor is preferably hermetically sealed in a package of the type previously described above.

In operation, the antennas 422 and 424 of the sensing device 410 receive an RF interrogation signal (i.e. an expanded, linear or nonlinear FM waveform) from a transceiver (not shown). The sensor may be located up to approximately 30 meters (100 feet) from the transceiver given the advantage of processing gain built into the input transducer.

The input transducer 414 compresses the interrogation signal into a narrow pulse on the order of several nanoseconds in width. This pulse is detected by the two sensing taps 416a and 416b. Each of the sensing taps 416a and 416b then produces a sample of the narrow pulse which is delivered to the antennas 422 and 424 along the connecting bus bars 418 and 420. The two sampled signals are separated in time by an amount corresponding to the separation between the taps 416a and 416b. This delay time between sampled pulses represents the nominal, unstrained reference delay time.

Since sensing device 410 is rigidly attached to a structure, it will necessarily be sensitive to any significant flex or strain in said structure. Any significant strain in the structure of interest which is transmitted to the substrate 412 of the sensing device 410, will create a change in the phase velocity, time delay and time separation between taps 416a and 416b, while changes in the time delay caused by changes in the ambient temperature may be calibrated out of the measurement. The resulting shift in pulse separation due to strain effects is remotely interrogated. It has been assumed, that for a given axial strain in the substrate 412 of the sensing device 410, there is a change in the phase velocity and time delay while the substrate remains stress free along all the other axes.

Strain is defined as $\Delta l/l_0$ or the ratio of the change in the length to the original length. Accordingly, the $\Delta l$ could be determined by measuring the change in delay time between taps by using the following formula: $\Delta l = v_a * \Delta t$, where $v_a$ is the acoustic velocity in the substrate and $\Delta t$ is the change in delay time between taps.

Figure 5A:
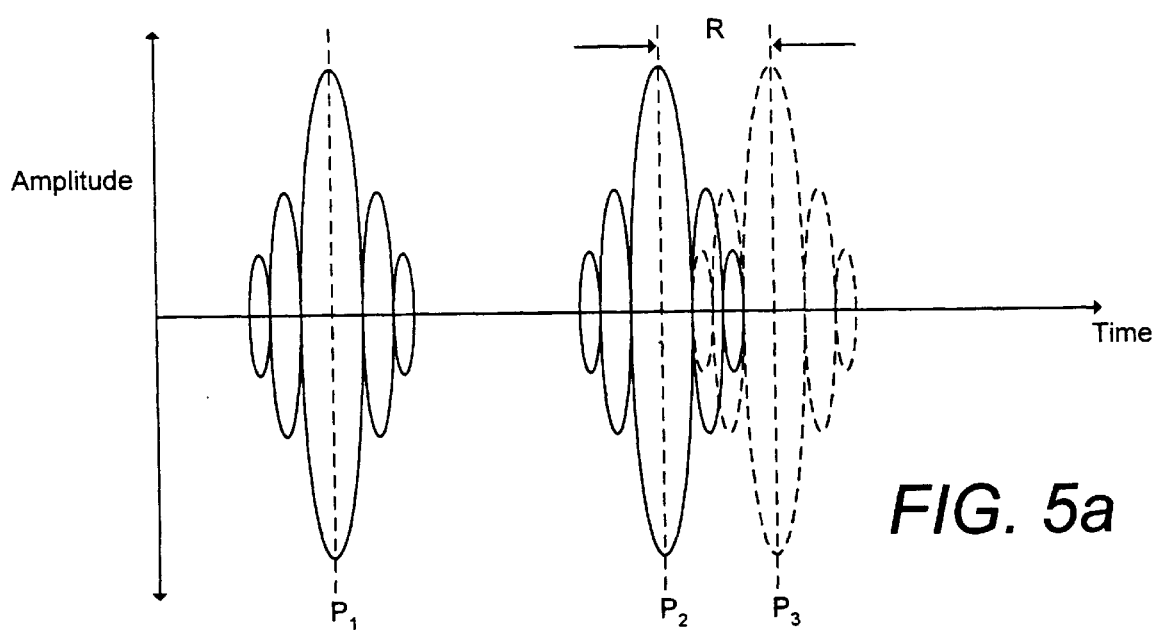
FIG. 5a is a graph showing strained and unstrained output is pulses at the output taps of the device shown in FIG. 5.

For a given compressed pulse width resulting from the input dispersive transducer 414, there is a minimum detectable resolution between pulses in close proximity. If it is assumed that the input transducer 414 has a bandwidth $\Delta f$ of 25 MHz, the compressed pulse width is approximately the reciprocal of the bandwidth, or 40 nanoseconds. In such an example, the pulse-on-pulse resolution (R) is about 2.5 (1/$\Delta f$) as shown in FIG. 5a, or about 100 nanoseconds. In FIG. 5a, $P_1$ shows a pulse at tap 416a, $P_2$ shows a pulse at tap 416b where there is no strain, and $P_3$ shows a pulse at tap 416b where there is strain. If the substrate is comprised of quartz which has a $\Delta v$ of $3.16 \times 10^5$ cm/sec, then the measurable strain 1 for this available resolution is:

$$\Delta l = (3.16 \times 10^5 \text{ cm/sec}) * (100 \times 10^{-9} \text{ sec}) = 3.16 \times 10^{-2} \text{ cm}$$

If the bandwidth of the input transducer 414 is increased to 100 MHz and 1/f=10 nanoseconds, then the pulse resolution becomes 2.5 * 10=25 nanoseconds and the measurable strain is:

$$\Delta l = (3.16 \times 10^5 \text{ cm/sec}) * (25 \times 10^{-9} \text{ sec}) = 79 \times 10^{-4} \text{ cm}$$

In such an example, the improved pulse resolution permits a smaller measurable strain.

A 100 MHz bandwidth sensor with a 20–23 dB processing gain capability should yield a practical system if a narrow-beam transmit antennas and low transmit power, e.g. 50–100 mW, are utilized.

Numerous modifications to and alternative embodiments of the present invention will be apparent to those skilled in the art in view of the foregoing description. Accordingly, this description is to be construed as illustrative only and is for the purpose of teaching those skilled in the art the best mode of carrying out the invention. Details of the structure may be varied substantially without departing from the spirit of the invention and the exclusive use of all modifications which come within the scope of the appended claims is reserved.

What is claimed is:

1. A passive surface acoustic wave sensing device for remotely sensing structural integrity within a physical structure, comprising:

a substrate having a polished upper surface, a bottom surface, a first end and a second end, said substrate being mounted to said physical structure;

a Radio Frequency (RF) circuit formed on the upper surface of said substrate for receiving and transmitting a RF signal;

an antenna means coupled to said RF circuit;

an input interdigital transducer means and an output interdigital transducer means disposed on said upper surface of said substrate, said input transducer means being located adjacent said first end of said substrate and said output transducer means being located adjacent said second end of said substrate, said input and output transducers being interconnected through a pair of parallel bus bars which extend therebetween on said upper surface of said substrate, said input transducer means providing a complementary first response upon receipt of a RF input signal from said antenna means, said output transducer means providing a second response upon receipt of said first response from said input transducer means, said output transducer means being adapted to transmit said second response to said antenna means;

means for carrying said first response to said output transducer means when said substrate is strained below a predetermined critical level; and means for preventing said first response from being transmitted to said output transducer means when said substrate is strained above said predetermined critical level.

2. The sensing device of claim 1, wherein said substrate is comprised of a piezoelectric material.

3. The sensing device of claim 1, wherein said carrying means extends across said upper surface of said substrate between said input and output transducer means.

4. The sensing device of claim 3, wherein said preventing means includes a notch formed across the width of said substrate in said bottom surface thereof, said substrate and said carrying means being adapted to fracture along said notch when said substrate is strained above said predetermined critical level.

5. A method of remotely sensing structural integrity within a physical structure utilizing a passive surface acoustic wave sensing device of the type which includes a piezoelectric substrate having an input transducer means and an output transducer means disposed thereon in a spaced apart relation, said method comprising the steps of:

rigidly mounting said surface acoustic wave sensing device to said physical structure so that said sensing device will be strained when said physical structure is strained;

transmitting a RF signal to said input transducer means;

transforming said RF signal into an acoustic wave having a distinct compressed pulse from said input transducer means;

transmitting said acoustic wave signal to said output transducer means along said substrate when said physical structure is strained below a predetermined level;

providing means for detecting receipt of said acoustic wave by said output transducer means; and preventing said acoustic wave signal from being transmitted to said output transducer means when said physical structure is strained above a predetermined level.

6. The sensing device of claim 1, wherein said output transducer means includes a plurality of output taps spaced at time-ordered intervals.

7. The sensing device of claim 1, wherein said output transducer means includes a plurality of output taps phase-coded at 0° and 180°.

8. The sensing device of claim 1, wherein said output transducer means includes a plurality of output taps spaced at time-ordered intervals and phase coded at 0° and 180°.

9. The sensing device of claim 1, wherein said input RF signal has a predetermined bandwidth and said first response is in the form of a pulse substantially equivalent to the reciprocal of said bandwidth of said RF signal.

10. A passive surface acoustic wave sensing device for remotely sensing structural integrity within a physical structure, comprising:

a substrate having an upper surface, a bottom surface, a first end and a second end, said substrate mounted to said physical structure so that when said structure is strained, said substrate is also strained;

an antenna means coupled to said substrate for receiving and transmitting a RF signal;

an interdigital input transducer and two spaced apart output sensing taps disposed on said upper surface of said substrate, said input transducer being located adjacent said first end of said substrate and said output sensing taps being located adjacent said second end of said substrate with said input transducer interconnected to said sensing taps through a pair of parallel bus bars which extend therebetween on said upper surface of said substrate;

said input transducer providing a complementary first response upon receipt of an input RF signal from said antenna means; and means for carrying said first response from said input transducer to said output sensing taps, each one of said output sensing taps providing an output response upon receipt of said first response emitted from said input transducer, each one of said output responses being transmitted to said antenna means via said carrying means, and each one of said output responses being separated in time by an amount corresponding to the separation between said output sensing taps so that any strain in said substrate will create a change in the phase velocity, time delay and time separation between said output sensing taps.

11. The sensing device of claim 10, wherein said substrate is comprised of a piezoelectric material.

12. The sensing device of claim 10, wherein said carrying means extends across said upper surface of said substrate between said input transducer and said output sensing taps.

13. The method of claim 5, wherein said method for preventing said acoustic wave from being transmitted to said output transducer means includes forming a physical break across said substrate between said input transducer means and said output transducer means.

14. A method of remotely sensing structural integrity within a physical structure utilizing a passive surface acoustic wave sensing device of the type which includes a piezoelectric substrate having an input transducer means and a pair of output transducer means disposed thereon in a spaced apart relation, said method comprising the steps of:

mounting said surface acoustic wave sensing device to said physical structure so that said sensing device will be strained when said physical structure is strained;

transmitting a RF signal to said input transducer means;

transforming said RF signal into an acoustic wave having a distinct compressed pulse from said input transducer means;

transmitting said acoustic wave to said output transducer means along said substrate when said physical structure is strained below a predetermined level;

modifying said delay time separation between output taps of said acoustic signals as it is transmitted along said substrate when said physical structure is strained above a predetermined level; and providing means for detecting the receipt of said acoustic signals by said output transducer means.

* * * * *